United States Patent [19]

Zeleznick et al.

[11] Patent Number: 5,002,973

[45] Date of Patent: Mar. 26, 1991

[54] STABILIZED SULFITE-FREE CATECHOLAMINE COMPOSITIONS

[75] Inventors: Lowell Zeleznick, Irvine; Allan M. Raff, Walnut Creek, both of Calif.

[73] Assignee: Dey Laboratories, Inc., Napa, Calif.

[21] Appl. No.: 426,495

[22] Filed: Oct. 23, 1989

Related U.S. Application Data

[63] Continuation-in-part of Ser. No. 138,629, Dec. 28, 1987, abandoned.

[51] Int. Cl.$^5$ ............................................. A61K 31/135
[52] U.S. Cl. .................................... 514/653; 514/654; 514/970; 514/973; 514/836
[58] Field of Search ............... 514/653, 654, 970, 973, 514/836; 424/45, DIG. 7

[56] References Cited

U.S. PATENT DOCUMENTS

| 2,698,823 | 3/1951 | Bersworth et al. | 424/DIG. 10 |
| 3,808,317 | 4/1974 | Hecht et al. | 514/973 |
| 3,966,905 | 6/1976 | Nite | 514/653 |
| 4,150,744 | 4/1979 | Fennimore | 206/205 |
| 4,164,570 | 8/1979 | Clough et al. | 514/653 |

FOREIGN PATENT DOCUMENTS 0150694  9/1981  Fed. Rep. of Germany ...... 514/973

OTHER PUBLICATIONS

Lachman–Antioxidants and Chelating Agents As Stabilizers in Liquid Dosage Forms, Drug Cosmet. Ind. 102(2), 43-45, 146-149, (1968).

Primary Examiner—Stanley J. Friedman
Assistant Examiner—Raymond J. Henley, III
Attorney, Agent, or Firm—Flehr, Hohbach, Test, Albritton & Herbert

[57] ABSTRACT

Novel catecholamine solutions for physiological uses are provided at a pH in the range of 1.0–5.0, comprising catecholamine, acetylcysteine, chelating agent and buffering agents. The compositions are stabilized from oxidation without the use of sulfites and are preferably administered by inhalation.

6 Claims, No Drawings

STABILIZED SULFITE-FREE CATECHOLAMINE COMPOSITIONS

This is a continuation-in-part of application Ser. No. 138,629 filed Dec. 28, 1987, now abandoned.

The present invention is directed to novel catecholamine compositions which are physiologically useful and which are stabilized from oxidation without the use of sulfites.

BACKGROUND OF THE INVENTION

Catecholamine compositions, such as epinephrine, are useful for various pharmaceutical purposes. As many types of organic compositions, catecholamines are sensitive to oxidation, and thus must be protected from oxidation in order to prolong shelf life and to prevent conversion to derivatives which are not as pharmaceutically effective and/or which may be harmful to the user. Oxidation of catecholamine can result in loss of titer of the active ingredient, formation of compounds which may have undesirable physiological effect and appearance of a dark color, which often makes the composition undesirable and unmarketable.

Many pharmaceutical compositions, including catecholamine compositions, have heretofore contained sulfites to stabilize the compositions from oxidation. However, use of sulfites has been found to be harmful and therefore there is a need to find methods for stabilizing catecholamines for their various physiological uses without the use of sulfites.

U.S. Pat. No. 3,966,905 discloses particular catecholamine solutions containing polyvinylpyrrolidone.

U.S. Pat. No. 3,091,569 discloses a mucolytic process comprising contacting a mucous with a certain class of N-acylated sulfhydrl compounds.

It is thus an object of the present invention to provide novel catecholamine-containing compositions which are sulfite-free.

It is a further object of the present invention to provide novel catecholamine solutions which are stabilized from oxidation and suitable for inhalation.

These and other objects will become apparent from the following description of the present invention to those of ordinary skill in the art.

SUMMARY OF THE INVENTION

The present invention provides physiologically useful sulfite-free catecholamine-containing aqueous compositions within a pH in the range of 0.1–5.0 consisting essentially of catecholamine, acetylcysteine (0.05–2.0% w/v), a chelating agent (0.01–0.25% w/v), and suitable buffering agents for maintaining pH.

DESCRIPTION OF THE SPECIFIC EMBODIMENTS

The aqueous compositions according to the present invention contain a pharmaceutically effective amount of a catecholamine. The amount which is present in the composition will depend upon the desired dosage unit for the particular use and the method of intended administration. Usually the composition will contain from about 0.1–10% weight/volume catecholamine. By the term catecholamine it is meant all of the compositions generically known as catecholamines, including compounds of the following formula:

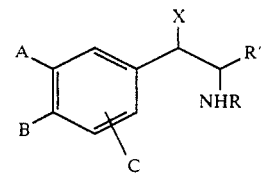

wherein X is hydrogen or hydroxyl, R and $R^1$ are hydrogen or alkyl of from 1-6 carbon atoms, A, B and C are independently selected from the group consisting of H, hydroxy, alkoxy of 1 to 6 carbon atoms and hydroxyalkyl of 1 to 6 carbon atoms, with the proviso that at least one of A, B, or C is hydroxy or alkoxy. Preferably $R^1$ is from 1-2 carbon atoms and R is hydrogen, methyl, ethyl, propyl or isopropyl. Preferably, A and B are both hydroxy and C is hydrogen. The alkoxy groups which may constitute A, B, or C include methoxy, ethoxy, n-propoxy, i-propoxy, n-butoxy, sec-butoxy, i-butoxy, t-butoxy, n-pentoxy and n-hexoxy. The hydroxy alkyl groups which may constitute A, B, or C include hydroxymethyl, 1-hydroxyethyl, 2-hydroxyethyl, 3-hydroxyprop-1-yl, 4-hydroxy-butyl, 5-hydroxypent-1-yl and 6-hydroxyhex-1-yl.

Particularly preferred catecholamines include those in which A and B are hydroxy and C is hydrogen, such as, epinephrine (X=OH, $R^1$=H, R=CH$_3$), and isoetharine hydrochloride (X=OH, $R^1$=ethyl, R=isopropyl).

A second component of the composition is acetylcysteine, preferably in an amount of 0.05–2.0% w/v, which serves as the the antioxidant. Acetylcysteine is physiologically acceptable and can be coadministered with the catecholamine by injection, topically by liquid or sprays or by inhalation, which is the preferred method of administration of the compositions according to the present invention. The dosages to be administered of the catecholamine (an active pharmaceutical component of the composition) are well known in the art. Particularly preferred uses include use as a spray or aerosol for opthalmological, nasal, or respiratory disorders.

A third component of the composition of the present invention is a chelating agent, particularly a chelating agent capable of binding heavy metals which are usually found in trace amounts in water. A preferred chelating agent is edetate disodium. Since only trace amounts of heavy metals will be present, small amounts of the chelating agent will be required, usually in the range of 0.01–0.25% w/v.

In order to obtain the desired pH range of 0.1–5.0, an appropriate buffer, preferably sodium citrate, adjusted with a small amount of mineral acid, such as hydrochloric acid, will be employed. This should be adjusted to preferably be within a range of 2.5–5.0, most preferably within a range of about 2.8–3.5.

The aqueous compositions according to the present invention will normally be relatively dilute aqueous solutions having about less than about 0.9 total weight percent of the above additives, usually less than about 1.5 total weight of the additives, and generally more than about 0.5 total weight percent of the additives. The amount of the catecholamine, which includes such compounds as epinephrine, levarterenol, nordefrin, and isoetharine hydrochloride, will normally be present in at least about 0.1% w/v, in general not exceeding 10% w/v percent. For compositions which are intended for inhalation, catecholamine will usually be present in about 0.08–1.0% w/v.

Pharmaceutical quality N-acetyl-L-cysteine is readily available commercially or may be prepared by known methods such as disclosed, for example, in U.S. Pat. No. 3,091,569 or by Pirie, et al., *Biochem. J.*, 27, 1716–18 (1933). Various catecholamines are also readily available from commercial sources and their methods of synthesis and purification are well known in the art.

The following example is presented by way of illustration and is not intended to limit the invention in any way.

EXAMPLE

Three samples of sulfite-free isoetharine solutions containing 1% acetylcysteine were stored at 37° C., and assayed at approximately four-week intervals for isoetharine activity (vs. the label claim and original potency at time zero) and pH. The three samples (each in triplicate) were stable at 37° C. for the three-month period of the test, which is equivalent to storage for two years at room-temperature (25° C.). In Table I, the assayed potency is given in percent of label claim, followed in parenthesis by percent potency of original value at time zero, calculated as $$\frac{\text{Value at time }(t) \times 100}{\text{Avg. of label claim values at time 0}}$$

TABLE I

Size of Package: 0.5 ML
Type of Package: 0.5 ML Polypropylene I.M. Vial

| AGE (month) | Isoetharine | | pH | CLARITY | COLOR | ODOR |
|---|---|---|---|---|---|---|
| BATCH A | | | | | | |
| LOWER SPEC | 92% LC | (0.92%) | 2.5 | | | |
| UPPER SPEC | 108% LC | (1.08%) | 5.5 | | | |
| LABEL CLAIM | 100% LC | (1.0%) | 4.0 | CLEAR | COLORLESS | TYPICAL |
| 0 | 100.0 | (100.0) | 3.0 | CLEAR | COLORLESS | TYPICAL |
| 0 | 98.9 | (100.0) | | | | |
| 0 | 101.0 | (100.0) | | | | |
| 1 | 101.0 | (101.0) | 3.0 | CLEAR | COLORLESS | TYPICAL |
| 1 | 104.0 | (104.0) | | | | |
| 1 | 102.0 | (102.0) | | | | |
| 2 | 99.5 | (99.5) | 2.9 | CLEAR | COLORLESS | TYPICAL |
| 2 | 101.0 | (101.0) | | | | |
| 2 | 99.3 | (99.3) | | | | |
| 3 | 100.0 | (100.0) | 3.0 | CLEAR | COLORLESS | TYPICAL |
| 3 | 101.0 | (101.0) | | | | |
| 3 | 99.4 | (99.4) | | | | |
| BATCH B | | | | | | |
| LOWER SPEC | 92% LC | (0.92%) | 2.5 | | | |
| UPPER SPEC | 108% LC | (1.08%) | 5.5 | | | |
| LABEL CLAIM | 100% LC | (1.0%) | 4.0 | CLEAR | COLORLESS | TYPICAL |
| 0 | 99.1 | (100.0) | 3.0 | CLEAR | COLORLESS | TYPICAL |
| 0 | 101.0 | (100.0) | | | | |
| 0 | 99.1 | (100.0) | | | | |
| 1 | 101.0 | (101.3) | 3.1 | CLEAR | COLORLESS | TYPICAL |
| 1 | 101.0 | (101.3) | | | | |
| 1 | 100.0 | (100.3) | | | | |
| 2 | 100.0 | (100.3) | 2.9 | CLEAR | COLORLESS | TYPICAL |
| 2 | 99.9 | (100.2) | | | | |
| 2 | 99.8 | (100.1) | | | | |
| 3 | 102.0 | (102.3) | 3.0 | CLEAR | COLORLESS | TYPICAL |
| 3 | 101.0 | (101.3) | | | | |
| 3 | 101.0 | (101.3) | | | | |
| BATCH C | | | | | | |
| LOWER SPEC | 92% LC | (0.92%) | 2.5 | | | |
| UPPER SPEC | 108% LC | (1.08%) | 5.5 | | | |
| LABEL CLAIM | 100% LC | (1.0%) | 4.0 | CLEAR | COLORLESS | TYPICAL |
| 0 | 103.0 | (100.0) | 3.1 | CLEAR | COLORLESS | TYPICAL |
| 0 | 104.0 | (100.0) | | | | |
| 0 | 101.0 | (100.0) | | | | |
| 1 | 99.1 | (96.5) | 3.2 | CLEAR | COLORLESS | TYPICAL |
| 1 | 99.9 | (97.3) | | | | |
| 1 | 99.1 | (96.5) | | | | |
| 2 | 102.0 | (99.4) | 3.1 | CLEAR | COLORLESS | TYPICAL |
| 2 | 102.0 | (99.4) | | | | |
| 2 | 102.0 | (99.4) | | | | |
| 3 | 102.0 | (99.4) | 3.1 | CLEAR | COLORLESS | TYPICAL |
| 3 | 104.0 | (101.3) | | | | |
| 3 | 103.0 | (100.3) | | | | |

The foregoing invention has been described in some detail by way of illustration for the purposes of clarity and understanding. However, it will be obvious that certain changes and modifications may be practiced within the scope of the appended claims.

What is claimed is:

1. A physiologically acceptable sulfite-free catecholamine-containing aqueous composition at a pH range of 2.8 to 3.5 consisting essentially of about 1.0% w/v of a catecholamine, from 0.05–2.0% w/v of acetylcysteine, 0.01–0.25% w/v edetate disodium, and buffer, wherein said catecholamine is a compound of the formula

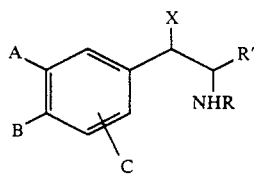

wherein X is hydrogen or hydroxyl, R and R¹ are hydrogen or alkyl of from 1-6 carbon atoms; A, B and C are independently selected from the group consisting of H, hydroxy, alkoxy of 1 to 6 carbon atoms and hydroxyalkyl of 1 to 6 carbon atoms with the proviso that at least one of A, B or C is hydroxy or alkoxy; said buffering agent is present in an amount sufficient to maintain the pH of said compositions within said range.

2. A composition according to claim 1 wherein said buffering agent comprises sodium citrate and hydrochloric acid.

3. A composition according to claim 2 wherein A and B are hydroxy and C is hydrogen.

4. A composition according to claim 3 wherein X is hydroxyl, R¹ is ethyl and R is isopropyl.

5. A composition according to claim 1 wherein A and B are hydroxy and C is hydrogen.

6. A composition according to claim 5 wherein X is hydroxyl, R¹ is hydrogen and R is methyl.

* * * * *